United States Patent

Kohlpaintner et al.

[11] Patent Number: 5,929,273
[45] Date of Patent: *Jul. 27, 1999

[54] PROCESS FOR PREPARING DIPHOSPINES LIGANDS AND CATALYSTS CONTAINING THE SAME

[75] Inventors: Christian W. Kohlpaintner, Corpus Christi, Tex.; Brian E. Hanson; Hao Ding, both of Blacksburg, Va.

[73] Assignee: Celanese International Corp, Dallas, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/634,534

[22] Filed: Apr. 18, 1996

Related U.S. Application Data

[62] Division of application No. 08/634,534, Apr. 18, 1996.

[51] Int. Cl.[6] .................................................. C07F 9/50
[52] U.S. Cl. .............................................. 562/35; 568/13
[58] Field of Search .................................. 568/13; 562/35

[56] References Cited

U.S. PATENT DOCUMENTS 5,693,868   12/1997   Sayo ............................................ 568/8

Primary Examiner—Robert Gerstl
Attorney, Agent, or Firm—James J Mullen

[57] ABSTRACT

The present invention provides novel water-soluble diphosphines having the formula

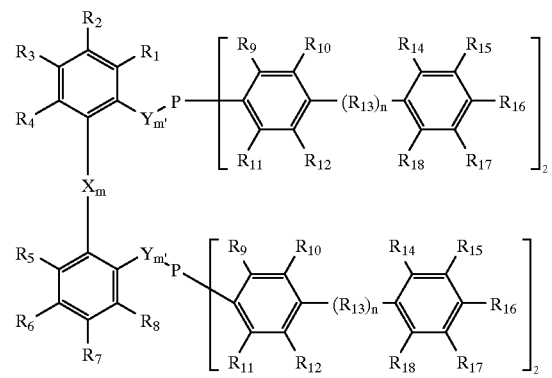

wherein X, Y, $R_{1-18}$ and n are defined herein, and which can be complexed with a transition metal to form a novel catalyst useful in such applications as hydroformylation.

3 Claims, No Drawings

PROCESS FOR PREPARING DIPHOSPINES LIGANDS AND CATALYSTS CONTAINING THE SAME

This application is a division of application Ser. No. 08/634,534, filed Apr. 18, 1996.

BACKGROUND OF THE INVENTION

1. Field of the Invention

The present invention is directed to novel water-soluble sulfonated aryl diphosphines, catalysts containing the same, processes for preparing such diphosphines and catalysts, and processes for using such catalysts.

2. General Background and Prior Art Problems

One of the major problems of homogeneous catalysis is the separation of catalyst from product. The lifetime of a catalyst in an industrial process is greatly affected by the means of separation. It has been shown that a two phase system with water soluble phosphines as ligands can be very effective to achieve easy recycling of catalysts. However, the reactivity of the water soluble catalyst is somewhat limited by the solubility of the organic substrate in aqueous phase. The synthesis of water soluble phosphines has reached a stage that it is possible now to tailor the structure of a phosphine for improved reactivity while retaining excellent water solubility for good catalyst separation.

A widely used method for synthesizing water soluble phosphines is direct sulfonation to introduce one or more sulfonate groups onto a phenyl ring bonded to phosphorus. Unfortunately the direct sulfonation often requires harsh conditions and long reaction times. The reaction produces significant amount of phosphine oxide along with phosphines with different degrees of sulfonation. All these complicate the purification of the sulfonated products and contribute to a poor yield of sulfonation products. Therefore, the conventional direct sulfonation is not very suitable for chiral and non-chiral water soluble phosphine synthesis, since a large portion of expensive chiral phosphine is going to be sacrificed in direct sulfonation. For this reason perhaps, the yields for the direct sulfonation of chiral phosphines such as BDPP and BINAP are not reported.

One of the most interesting chiral biphosphines is (R)-(+)- and (S)-(−)-2,2'-Bis(diphenylphosphino)-1,1'-binaphthyl, BINAP. It shows exceptional enantioselectivity for asymmetric hydrogenations. The direct sulfonation of BINAP results in a mixture of phosphines with various degrees of sulfonation. The uncertainty of the sulfonated sites causes difficulties for characterization of the ligand and its metal complexes.

Thus, there is a need for new compounds which are water soluble, exhibit outstanding surface active properties in two phase catalysis, particularly in the area of two phase hydroformylation of olefins such as 1-octene, and are easily accessible by mild sulfonation conditions.

DESCRIPTION OF THE PRIOR ART

The following prior art references are disclosed in accordance with the terms of 37 CFR 1.56, 1.97, and 1.93.

U.S. Pat. No. 5,057,618 discloses complex compounds containing sulfonated phenyl phosphines.

U.S. Pat. No. 5,274,183 discloses water-soluble sulfonated diphosphines.

Other references pertinent to diphosphine ligands, processes for preparing the same, and catalysts containing the same include:

1. W. A. Herrmann, C. W. Kohlpaintner, *Angew. Chem. Int. Ed. Engl.*, 1993, 32, 1524–1544.
2. R. Noyori, *Chem. Soc. Rev.*, 1989, 18, 187.
3. R. Noyori, M. Kitamura, *Modern Synthetic Methods*, Vol. 5, R. Scheffold ed., Berlin: Springer-Verlag, 1989, 115–198.
4. R. Noyori, *Chemtech*, June 1992, 360–367.
5. Y. Amranni, L. Lecomte, D. Sinou, J. Bakos, I. Toth, B. Heil, *Organometallics*, 1989, 8, 542–547.
6. K. Wan, M. E. Davis, *J. C. S., Chem. Commun.*, 1993, 1263.
7. H. Ding, B. E. Hanson, T. Bartik, B. Bartik, *Organometallics*, 1994, 13, 3761.
8. H. Ding, B. E. Hanson, *Angew. Chem. Int. Ed. Engl.*, 107, 1728 (1995).
9. A. S. C. Chan, *Chemtech*, March 1993, 47–51.
10. N. Sayo, H. Kumobayashi, S. A. Kutagawa, R. Noyori, H. Takaya, EP-A-0 295 890 (19 6 1987).
11. W. S. Knowles, *Acc. Chem. Res.*, 1983, 16, 106.
12. W. S. Knowles, W. O. Christopher, K. E. Koening, C. F. Hobbs, *Adv. Chem. Ser.*, 1982, 196, 325.
13. T. Ohta, H. Takaya, M. Kitamura, K. Nagai, R. Noyori, *J. Org. Chem.*, 1987, 52, 3174.
14. M. Fiorini, G. M. Giongo, *J. Mol. Catal.*, 1979, 5, 303.
15. M. Fiorini, G. M. Giongo, ibid, 1980, 7, 411.
16. J. E. Babin, G. T. Whiteker, *World Patent.* WO 93/03839, 1993.
17. H. Ding, B. E. Hanson, *J. C. S., Chem. Commun.*, 1994, 2747.
18. M. Vondenhof and J. Mattay, *Tetrahedron lett.*, 1990, 31, 985.
19. *J Org. Chem.*, D. Cai, J. F. Payack, D. R. Bender, D. L. Hughes, T. R. Verhoeven and P. J. Reider, 1994, 59, 7180.
20. T. Maninaran, T -C. Wu, W. D. Klobucar, C. H. Kolich, G. P. Stahly, F. R. Fronczek and S. E. Watkins, *Organometallics.* 1993, 12, 1467.
21. K. Wan and M. E. Davis, *J Catal.*, 1994, 148, 1.
22. D. Cai, J. F. Payack, D. R. Bender, D. L. Haghes, T. R. Verhoeven, P. J. Reider, *J. Org. Chem.*, 1994, 59, 7180.

All of the above cited prior art and any other references mentioned herein are incorporated herein by reference in their entirety.

SUMMARY OF THE INVENTION

The present invention provides novel aryl diphosphines having the formula

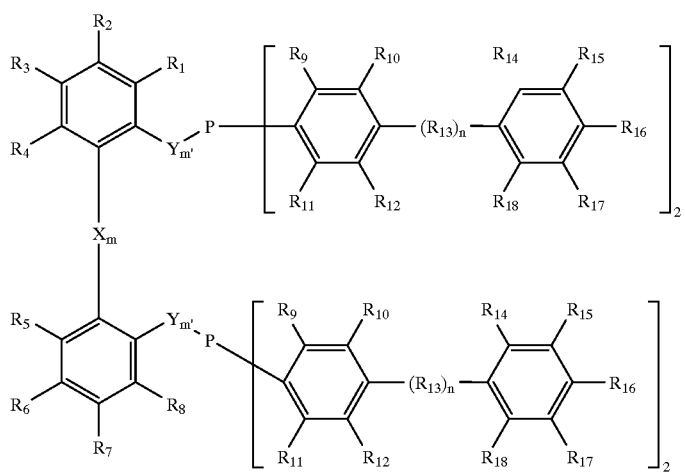

(I)

wherein X, Y, $R_{1-18}$, m, m' and n are defined herein, and which can be complexed with a transition metal to form a novel catalyst useful in such applications as hydroformylation.

DETAILED DESCRIPTION OF THE INVENTION

The present invention provides, in part, a novel aryl diphosphine having the formula

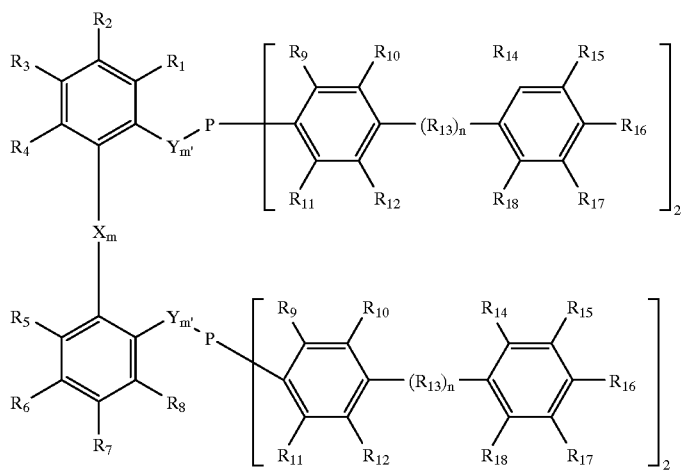

(I)

wherein (a) X and Y are each independently selected from the group consisting of alkyl $C_1$–$C_{20}$, alkenyl $C_1$–$C_{20}$, alkynyl $C_1$–$C_{20}$, phenyl, naphthyl, —NR— (where R is H, alkyl $C_1$–$C_{20}$ and phenyl), oxygen and sulfur; (b) m and m' are each separate integers of 0 or 1; (c) $R_1$–$R_8$ are each independently selected from the group consisting of hydrogen, halogen, nitro, amino, alkyl $C_1$–$C_{20}$, alkoxy, hydroxy, —C(O)—OR, —CN, —$SO_3M$, —$N^{\oplus}(R)_3X^{\ominus}$ (where $X^{\ominus}$ is a halide), and aryl; (d) $R_1$ and $R_2$, $R_2$ and $R_3$, $R_3$ and $R_4$, $R_5$ and $R_6$, $R_6$ and $R_7$, $R_7$ and $R_8$ may also (in addition to the above) form a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; (e) $R_9$–$R_{12}$ and $R_{14}$–$R_{18}$ are each independently selected from the group consisting of hydrogen, halogen, —$SO_3M$ where M is an alkali metal (e.g. Na, K, Li, Rb, Cs), alkaline earth metals such as Mg and Ca, and $N(R)_4^{\oplus}$ (where R is H, alkyl $C_1$–$C_{20}$, phenyl), alkyl $C_1$–$C_{20}$, —$CO_2M$, —$N^{\oplus}(R)_3X^{\ominus}$ (where $X^{\ominus}$ is a halide), —CN, —OR, —C(O)—OR, and —$P(R)_2$, where R is H, alkyl $C_1$–$C_{20}$, and phenyl; (f) $R_{13}$ is selected from the group consisting of a straight chain or branched chain alkyl $C_1$–$C_{20}$, alkenyl $C_1$–$C_{20}$, alkynyl $C_1$–$C_{20}$, phenyl, naphthyl, anthracyl, and substituted phenyl, naphthyl, and anthryl; and (g) n is an integer from 0 to 20.

In formula I above, the substituents on the phenyl, naphthyl, anthracyl and the cyclic ring are selected, for example, from the group consisting of hydrogen, nitro, halogen, alkoxy, alkyl $C_1$–$C_{20}$, carboxylate, amino, amide, silyl, and siloxyl.

In order to provide the greatest water solubility, at least one of $R_1$–$R_{12}$ and $R_{14}$–$R_{18}$ is —$SO_3M$.

In the above definitions of X, Y, and $R_1$–$R_{18}$, the term halogen includes chlorine, fluorine, bromine and iodine. The term alkyl includes straight and branch chained saturated hydrocarbon radicals having from 1 to 20 carbon atoms such as, for example, methyl; ethyl; 1-methylethyl; 1,1,-dimethylethyl; propyl; 2-methylpropyl; butyl; pentyl; hexyl and the like. The term alkoxy includes the alkyl definition above plus the oxygen atom e.g. methoxy, ethoxy, isopropoxy, tert-butoxy, and the like. Term aryl includes phenyl, naphthyl, anthryl, phenanthryl and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

In another facet of the present invention, the ligands/diphosphines of formula I are complexed with a transition metal (M') to yield new catalysts having the formula wherein X, Y, $R_{1-18}$, M, m, m' and n are the same as described in formula I above, and M' is selected from the group consisting of chromium, manganese, iron, cobalt, nickel, copper, molybdenium, technetium, ruthenium, rhodium, palladium, silver, cadmium, tungsten, rhenium, osmium, indium, platinum, gold, and mercury; L is any ligand which can be bound to M'; and x is an integer of 0 to 7.

Formula II shows that M' is complexed with both phosphorus atoms in a bidentate form; however, it is also within the scope of the present invention that the metal M' is only complexed with one phosphorus atom in a monodentate form as shown below:

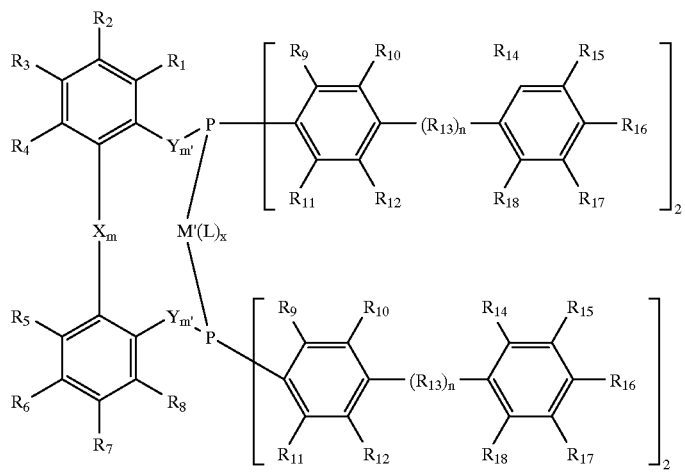

(II)

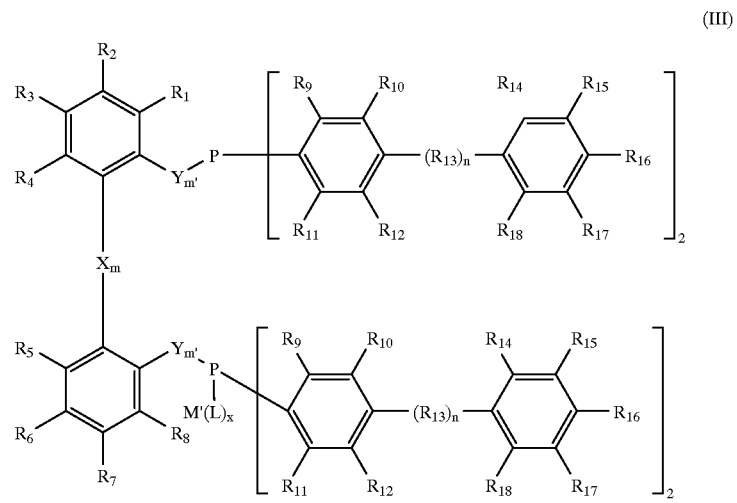

(III)

wherein X, Y, $R_{1-18}$, M, M', m, m', n, L and x are the same as in formula II.

To enhance the formation of compounds falling within formula (III), one phosphorus atom can be oxidized, sulfidized, or quaternized to prevent coordination.

Thus the single P-atom moiety can have the partial formula

(a)

(b)

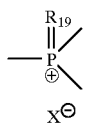

(c)

wherein R is alkyl $C_1$–$C_{20}$ (straight or branched chain), phenyl (substituted or unsubstituted) and naphthyl (substituted or unsubstituted); and $X^\ominus$, in this case, is a halide such as F, Br, I, and Cl, or tosylate ($=CF_3SO_3^\ominus$).

Specific categories of the novel catalysts where the non-monodentate phosphorus atom is oxidized, sulfidized, or quaternized are shown below:

(a)

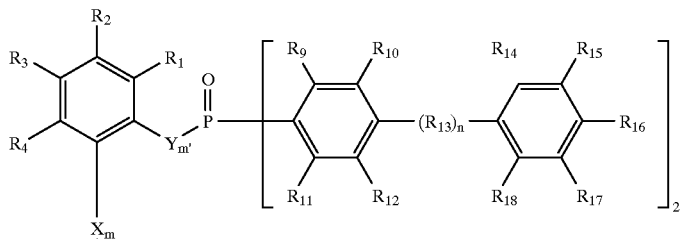

(IV)

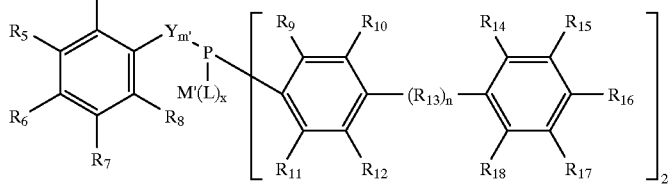

(b)

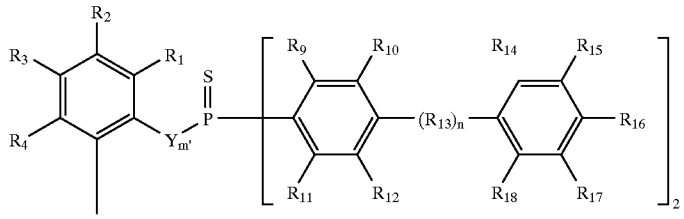

(V)

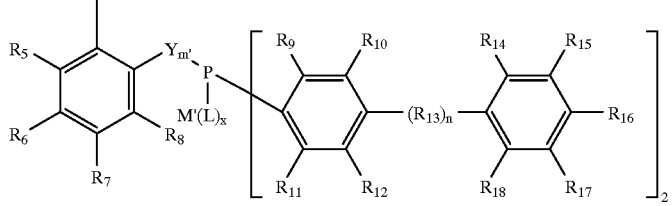

(c)

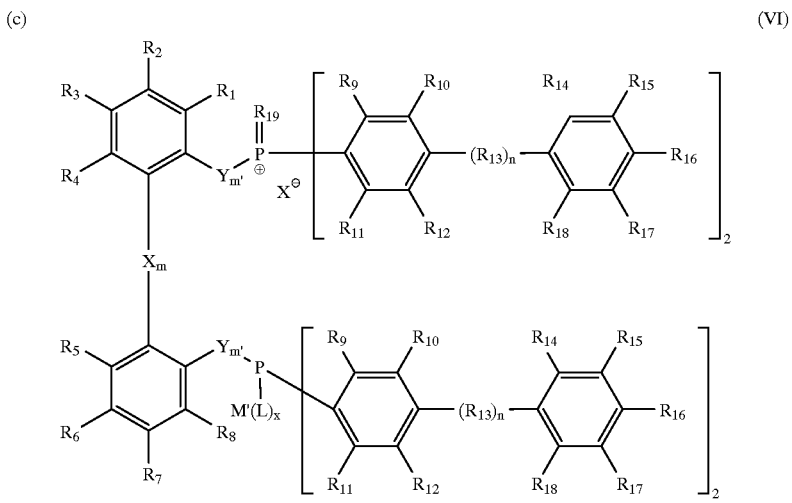

(VI)

In these formulae, L is any ligand which can be complexed with M', i.e. bound to the central atom in the complex compound. Typical ligands which fall within this category include, without limitiation, CO, NO, $PF_3$, $H_2O$, S, halogen (Cl, F, Br, I), $PF^-_6$, $CN^-$, $BF^-_4$, hydrides, π-aromatic ligands such cyclopentadienyl, π-olefin ligands such as cyclooctadiene, π-acetylene ligands such as diphenylacetylene, and other phosphine ligands.

In these formulae, M' represents any metal, i.e. a transition metal which can be bound or complexed with the phosphorus atom(s). Such metal is from the groups IB, VII A and VIII A of the Periodic Table (IuPAC version numbers group 1–18). Thus, M' includes, without limitation chromium, manganese, iron, cobalt, nickel, copper, molybdenum, technetium, ruthenium, rhodium, palladium, silver, cadmium, tungsten, rhenium, osmium, indium, platinum, gold, and mercury.

In general, the novel aryl diphosphine ligands are prepared by a process which comprises the steps of (a) subjecting an arylphosphine halide to metallation conditions including suitable temperature and pressure to form an arylphosphinide, and (b) subjecting said arylphosphinide to coupling conditions, including suitable temperature and pressure, in the presence of an organic halide to form said aryl diphosphine.

The starting material is an aryl-phosphine halide having the formula

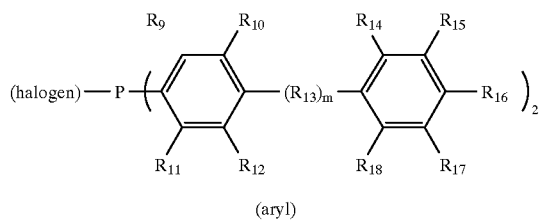

(aryl)

wherein $R_9$–$R_{18}$ and n are the same as disclosed for formula I above, except —$SO_3M$ is not present.

The metallation conditions are those which promote the complexing of a metal from Group I and Group II of the Periodic Table of Elements to the phosphorus atom. The metal is, for example, lithium, sodium, potassium, rubidium, cesium, magnesium, and calcium. The molar ratio of metal to phosphine halide can be any amount as long as the reaction proceeds to yield the desired result. In general however, such ratio is about 2:1. The temperatures and pressures are not critical, however, the temperature range is from about 0° C. to about 100° C., or greater. The pressure can be sub-atmospheric, atmospheric or super-atmospheric. The reaction time is not critical.

Thus, this metallation proceeds as follows:

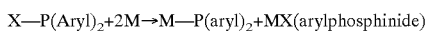

where X is a halide or another electron withdrawing group (EWG) and M is a metal.

The end result, as shown above, is an arylphosphinide. This arylphosphinide is then subjected to coupling conditions as shown below:

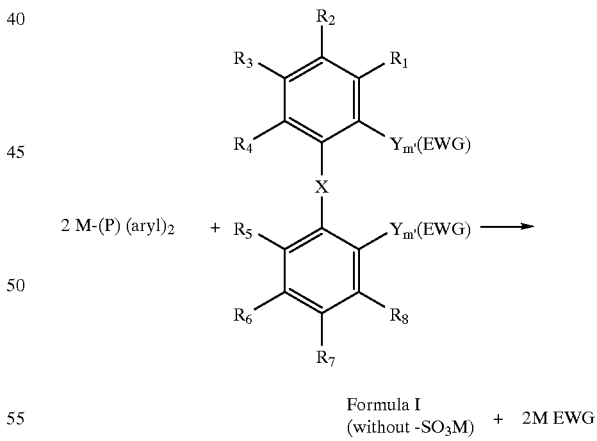

EWG is an electron withdrawing group such as a halide like Br or —$OSO_2R$ where R is alkyl $C_1$–$C_{20}$, preferably fluorinated such as $CF_3$, $C_2F_5$ etc.

The coupling conditions are not critical and can be any temperature and pressure as long as the desired end result is achieved. The temperature range is generally from about 0° C. to about 100° C. or greater. The pressure can be sub-atmospheric, atmospheric, or super-atmospheric. The reaction time is not critical. The halide is Cl, Br, F, or I, and generally is Br.

In another facet of the present invention, the diphosphine can also be prepared by reacting the phosphine H—P(aryl)$_2$ with

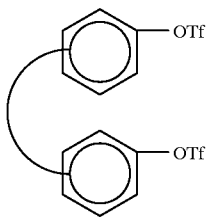

to yield the diphosphine with the assistance of a coupling catalyst like NiCl$_2$ (dppe), where

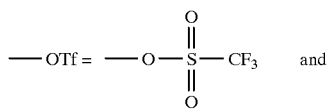

(dppe) is C$_6$H$_5$)$_2$P—CH$_2$—CH$_2$—P(C$_6$H$_5$)$_2$, Bis(diphenylphosphino)ethane. Thus, an equation for this reaction is as follows:

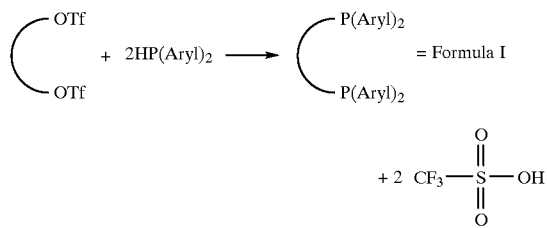

In order to provide the aryl diphosphine with water-soluble characteristics, the diphosphine of Formula (I), without the —SO$_3$M group, is subjected to acid sulfonation and base conditions as shown below:

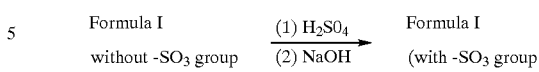

The acid, such as H$_2$SO$_4$, provides the —SO$_3^\ominus$ groups and the base, such as NaOH, provides a metal, M, such as sodium. In this fashion, it has unexpectedly been found that the sulfonation can be carried out in an easy manner (i.e. without significant oxidation or degradiation reactions at very mild conditions), as compared to the prior art, and that the end result is a water-soluble aryl diphosphine which can be used (along with a metal for complexing to form a catalyst) in numerous organic processes. The temperatures, pressures and reaction times of this sulfonation are not critical.

It is to be understood that the processes as described above can employ a solvent to facilitate the reaction mechanism. Such solvents are, in general, organic and include, without limitation, THF, Et$_2$O, alkanes and/or mixtures thereof.

Scheme 1 shows an example of the preparation of a water-soluble aryl diphosphane ligand, 2,2'-Bis{di[p-(3-p-sulfonatophenylpropyl)phenyl]phosphinomethyl}-1,1'-biphenyl (BISBI-C$_3$-TS).

Scheme 1

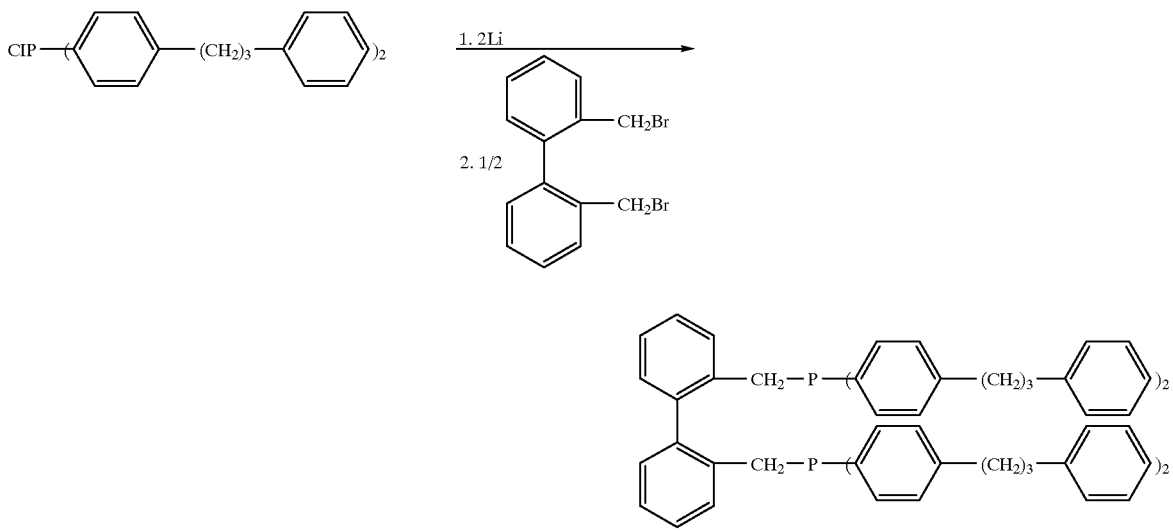

-continued

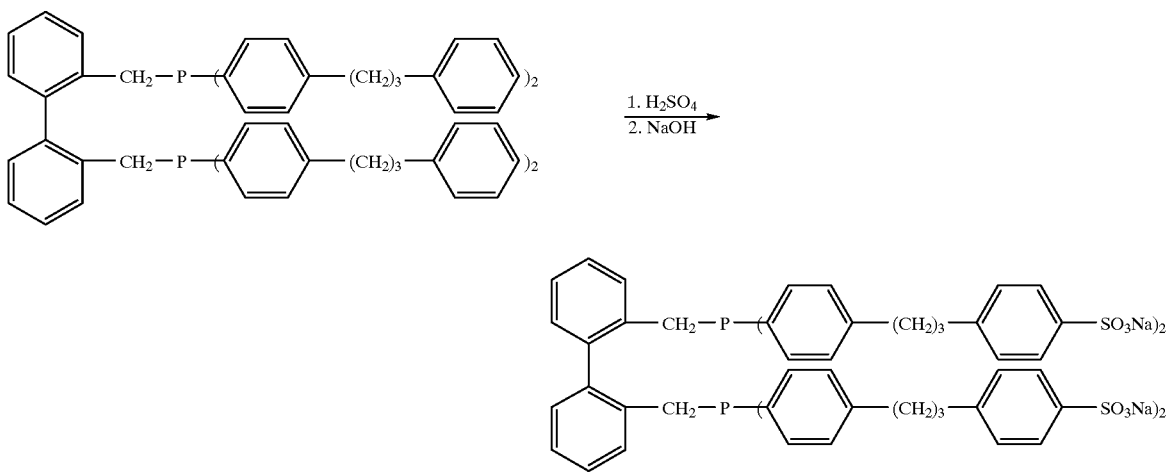

The novel catalysts sometimes referred to as a "metal-ligand complex catalysts" of the present invention are prepared either in situ or by reacting the water-soluble aryl diphosphine ligand with, for example, Rh(CO)$_2$ acac (acac= acetylacetonate) in an organic liquid/solvent such as methanol.

Although the novel catalysts have a wide variety of applications and uses in numerous organic processes, one facet of the present invention relates to asymmetric synthesis in which, e.g. a prochiral or chiral compound is reacted in the presence of optically active, metal-ligand complex catalyst, in enantiomerically active form, to produce an optically active product.

Specifically, it has been unexpectedly found that the novel catalysts, disclosed in the earlier part of this specification, can effect asymmetric synthesis in various processes with various substrates to produce a material which is optically active.

The asymmetric synthesis processes of this invention are useful for the production of numerous optically active compounds, e.g., aziridines, cyclopropanes, aldehydes, alcohols, ethers, esters, amines, amides, carboxylic acids and the like, which have a wide variety of applications.

This part of the subject invention encompasses the carrying out of any known conventional synthesis in an asymmetric fashion with the novel optically active metal-ligand complex catalyst as disclosed herein. Some processes of this invention stereoselectively produce an enantiomer.

The permissible achiral, prochiral or chiral starting material reactants encompassed by part of the processes of this invention are, of course, chosen depending on the particular synthesis desired. Such starting materials are well known in the art and can be used in conventional amounts in accordance with conventional methods. Illustrative starting material reactants include, for example, substituted and unsubstituted aldehydes (intramolecular hydroacylation, aldol condensation), prochiral olefins (hydroformylation, hydrogenation, hydrocyanation, hydrosilylation, aziridination, hydroamidation, aminolysis, cyclopropanation, hydroboration, Diels-Alder reaction, codimerization), ketones (hydrogenation, hydrosilylation, aldol condensation, transfer hydrogenation, allylic alkylation), epoxides (hydrocyanation, nucleophilic ring opening reaction), alcohols (carbonylation) acyl and aryl chlorides (decarbonylation), a chiral Grignard reagent (Grignard cross coupling) and the like.

The novel catalysts of the present invention thus have utility in a wide variety of chemical processes, and particularly, in asymmetric synthesis reaction which include, without limitation; hydroxylation; cyclopropanation; aziridination; Diels-Alder reactions; cycloaddition, Michael addition; Aldol reaction; hydroboration; olefin and ketone hydrosilylation; hydrocyanation; addition of Grignards or organometallics to aldehydes and ketones; allylic alkylation; Grignard cross coupling; kinetic resolution; hydroamidation; olefin isomerization; aminolysis; hydrogenation; hydroformylation; and hydrocarboxylation.

The amount of catalyst in the reaction medium of a given process of this invention need only be that minimum amount necessary to catalyze the particular organic syntheses process desired. In general, concentrations in the range of from about 1 ppm to about 10,000 ppm, based on the starting reactant, should be sufficient for most syntheses processes. For example, in the catalyzed processes of this invention, it is generally preferred to employ from about 10 to 1000 ppm and more preferably from 25 to 750 ppm.

The process conditions employable in the organic processes of this invention are, of course, chosen depending on the particular organic syntheses desired. Such process conditions are well known in the art. All of the organic syntheses processes of this invention can be carried out in accordance with the conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference in their entirety. Depending on the particular process, operating temperatures can range from about −80° C. or less to about 500° C. or greater and operating pressures can range from about 1 psia or less to about 10,000 psia or greater.

The reaction conditions of effecting, for example, the processes of this invention may be those heretofore conventionally used and may comprise a reaction temperature of from about −25° C. or lower to about 200° C. or higher and pressures ranging from about 1 to about 10,000 psia. Moreover, while such other syntheses may be performed under their usual conditions, in general, it is believed that they may be performed at lower temperatures than normally preferred due to the presence of the metal-ligand complex catalysts.

In general, the processes of this invention may be conducted at a reaction temperature from about −25° C. or lower to about 200° C. The preferred reaction temperature employed in a given process will, of course, be dependent upon the particular starting material and metal-ligand complex catalyst employed as well as the efficiency desired.

The processes are conducted for a period of time sufficient to produce the desired products. The exact time employed is dependent, in part, upon factors such as temperature, nature, and proportion of starting materials, and the like. The reaction time will normally be within the range of from about one-half to about 200 hours or more, and preferably from less than about 1 to 10 hours.

The processes of this invention may be conducted in the presence of an organic solvent for the metal-ligand complex catalyst. Depending on the particular catalyst and reactants employed, suitable organic solvents include, for example, alcohols, alkanes, alkenes, alkenes, ethers, aldehydes, ketones, esters, acids, amides, amines, aromatics, and the like. Any suitable solvent which does not unduly adversely interfere with the syntheses process can be employed and such solvents may include those heretofore commonly employed in known metal catalyzed processes. Increasing the dielectric constant or polarity of a solvent may generally tend to favor increased reaction rates.

Mixtures of one or more different solvents may be employed if desired. It is obvious that the amount of solvent is not critical to the subject invention and need only be that amount sufficient to provide the reaction medium with the particular metal concentration desired for a given process. In general, the amount of solvent when employed may range from about 5% by weight up to about 95% by weight or more, based on the total weight of the reaction medium.

The processes of this invention can provide optically active products by having very high enantioselectivity and regioselectivity. Enantiomeric excesses of preferably greater than 50% can be obtained by the processes of this invention. The processes of this invention can also be carried out at highly desirable reaction rates suitable for commercial use.

The desired products may be recovered in most cases by phase separation. Other separation methods include solvent extraction, crystallization, distillation, vaporization, wiped film evaporation, falling film evaporation, and the like. It may be desired to remove the products from the reaction systems as they are formed through the use of trapping agents as described in WO patent 88/08835.

The optically active products produced by the asymmetric syntheses processes of this invention can undergo further reaction(s) to afford desired derivatives thereof. Such permissible derivitization reactions can be carried out in accordance with conventional procedures known in the art. Illustrative derivitization reactions include, for example, esterification, oxidation of alcohols to aldehydes, N-alkylation of amides, addition of aldehydes to amides, nitrile reduction, acylation of ketones by esters, acylation of amines, and the like.

Illustrative of suitable reactants in effecting the processes of this invention include by way of example:

| | |
|---|---|
| AL | alcohols |
| PH | phenols |
| THP | thiophenols |
| MER | mercaptans |
| AMN | amines |
| AMD | amides |
| ET | ethers |
| EP | epoxides |
| ES | esters |
| H | hydrogen |
| CO | carbon monoxide |
| HCN | hydrogen cyanide |
| HS | hydrosilane |
| W | water |
| GR | grignard reagent |
| AH | acyl halide |
| UR | ureas |
| OS | oxalates |
| CN | carbamates |
| CNA | carbamic acids |
| CM | carbonates |
| CMA | carbonic acids |
| CA | carboxylic acids |
| ANH | anhydrides |
| KET | ketones |
| OLE | olefins |
| ACE | acetylenes |
| HAL | halides |
| SUL | sulfonates |
| ALD | aldehydes |
| NIT | nitriles |
| HC | hydrocarbons |
| DZ | diazo compounds |
| BOR | boranes |
| ESE | enol silyl ethers |
| SUD | sulfides |

Illustrative of suitable products prepared by the asymmetric syntheses processes of this invention include by way of example:

| | |
|---|---|
| AL | alcohols |
| PH | phenols |
| THP | thiophenols |
| MER | mercaptans |
| AMN | amines |
| AMD | amides |
| ET | ethers |
| ES | esters |
| H | hydrogen |
| CO | carbon monoxide |
| SI | silanes |
| UR | ureas |
| OX | oxalates |
| CN | carbamates |
| CNA | carbamic acids |
| CM | carbonates |
| CMA | carbonic acids |
| CA | carboxylic acids |
| ANH | anhydrides |
| KET | ketones |
| OLE | olefins |
| ACE | acetylenes |
| HAL | halides |
| ALD | aldehydes |
| NIT | nitriles |
| HC | hydrocarbons |
| CYP | cyclopropanes |
| ABR | alkylboranes |
| ADL | aldols |
| AZ | aziridines |

Illustrative of reactions encompassed within the scope of this invention include, for example, the following reactant/product combinations:

| REACTANT(S) | PRODUCT(S) |
|---|---|
| OLE, CO, H | ALD |
| OLE, CO, H | CA |
| ALD | KET |

-continued

| REACTANT(S) | PRODUCT(S) |
|---|---|
| OLE, ALD | KET |
| OLE, HC | HC |
| OLE, CO | CA |
| OLE, CO, AMN | AMD |
| OLE | AZ |
| OLE, CO, AL | ES |
| KET, H | AL |
| EP, H | AL |
| OLE, AMN | AMN |
| OLE, AL | ET |
| AL, CO | CA |
| AL | ALD |
| OLE, HCN | NIT |
| OLE, HS | SI |
| OLE, CO, W | CA |
| OLE | OLE |
| GR | HC |
| AH | HAL |
| OLE, H | HC |
| OLE, BOR | AL |
| OLE, BOR | ABR |
| OLE, DZ | CYP |
| KET, AL | AL |
| ALD, ESE | ADL |
| KET, ESE | ADL |
| KET, HS | AL |
| EP, CO, H | ALD |
| EP, HCN | NIT |
| ALD | CA |

As indicated above, the processes of this invention can be conducted in a batch or continuous fashion, with recycle of unconsumed starting materials if required. The reaction can be conducted in a single reaction zone or in a plurality of reaction zones, in series, or in parallel, or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal-ligand complex catalyst. When complete conversion is not desired or not obtainable, the starting materials can be separated from the product and the recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Finally, the products of the process of this invention have a wide range of utility that is well known and documented in the prior art, e.g. they are especially useful as intermediates for pharmaceuticals, flavors, fragrances, agricultural chemicals, and the like. Illustrative therapeutic applications include, for example, non-steroidal anti-inflammatory drugs, ACE inhibitors, beta-blockers, analgesics, bronchodilators, spasmolytics, antihistamines, antibiotics, antitumor agents, and the like.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

General Aspects of the Synthesis of Surface Active Phosphines

The overall scheme of preparing the desired compounds is set forth in Scheme 2 as a compliment to Scheme 1. The specific steps are indicated in Scheme 2 and are thereafter set forth in the indicated paragraphs with the experimental data. The compound numbers are shown with double underlining. All syntheses were done under an atmosphere of nitrogen or argon. Solvents were distilled under nitrogen prior to use. Concentrated sulfuric acid for the sulfonation of phosphines was used as received. 2,2'-bis(trifluoromethanesulfonyloxy)-1,1'-binaphthalene was made by a literature method [18].

Scheme 2

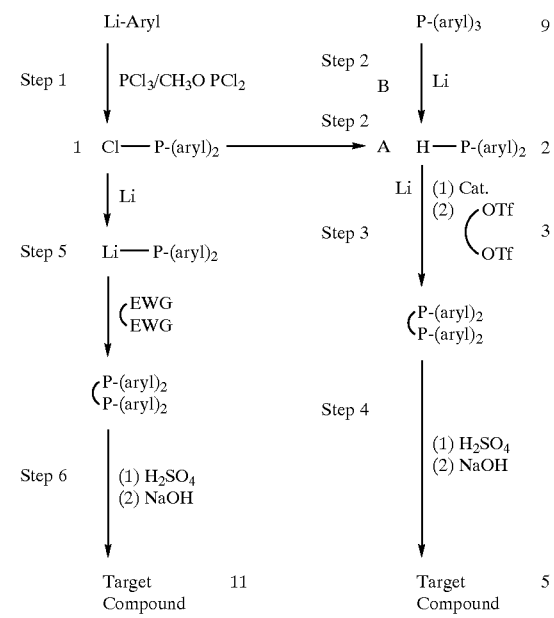

EWG means electron withdrawing group
Example 1 encompasses steps 1, 2a & b, 3 and 4
Example 3 encompasses steps 1, 5 and 6

EXAMPLE 1

Step 1 (Scheme 2)

The Synthesis of Di[p-(3-phenylpropyl)phenyl]chlorophosphine, 1 p-(3-phenylpropyl)phenyllithium (8.1 g, 40 mmol) in 150 ml solvent (Et$_2$O/THF 1/1) was added dropwise to CH₃OPCl₂ (2.66 g, 20 mmol) in 70 ml solvent (Et₂O/THF 1/1) at −70° C. The addition was completed in 2 h. The reaction mixture was stirred overnight at room temperature and then brought to reflux for 2 h. The precipitate was filtered and the solvent of the solution was removed by applying vacuum. PCl₃ (15 ml) was added to the resulting viscous oil and stirred for 24 h. Then the mixture was kept at 70° C. and 1 mm Hg for 2 h to remove excess PCl₃ and byproduct. The product, di[p-(3-phenylpropyl)phenyl] chlorophosphine, was obtained as a pale yellow viscous oil with 90% yield. The product was characterized by ³¹P NMR. 83.6

Step 2 A (Scheme 2)

The Synthesis of Di[p-(3-phenylpropyl)phenyl] phosphine, 2

Di[p-(3-phenylpropyl)phenyl]chlorophosphine 1 (6.0 g, 13.1 mmol) was dissolved in 150 ml THF and Li (0.185 g, 26.2 mmol) was chopped directly into the reaction flask under Ar. A deep red solution was resulted in 10 min and all the lithium was consumed in 4 h. The solvent was removed by vacuum and 100 ml diethyl ether was added. The organic phase was washed 3×20 ml H₂O and dried over MgSO₄. Ether was then removed by vacuum and the final product was obtained as a pale yellow oil with quantitative yield. 2 was characterized by ³¹P NMR. −42.5, $^1J_{H-P}$=211 Hz

Step 2 B (Scheme2)

Finely chipped lithium metal (0.14 g, 0.02 mol) is suspended in 10 mL dry THF and tris-p-(3-phenylpropyl) phenylphosphine 9 (6.2 g, 0.01 mol) in 100 mL THF is added from a droppping funnel over a period of about 10 minutes with vigorous stirring. The resulting deep red solution is stirred at room temperature for an additional 2 hours. Tertiary butylchloride (0.93 g, 0.01 mol) is added and the reaction mixture is brought to reflux for 15 minutes. The volume of the solution is reduced to about 10 mL and 80 mL dry degassed pentane is added. The reaction flask is then cooled to −78° C. to yield a dark red viscous residue and a colorless liquid. After decanting the colorless liquid, the residue 2 is redissolved in 50 mL THF {³¹P NMR (THF): −25.97}. The resulting anion can be used in subsequent synthesis that call for ⁻PAr₂, for instance in Step 5 (Scheme 2).

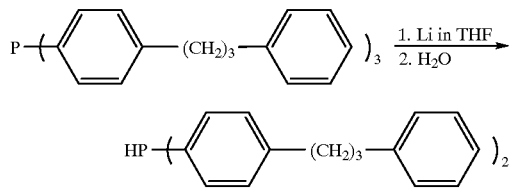

Step 3 (Scheme 2)

The Synthesis of 2,2'-Bis{di[p-(3-phenylpropyl) phenyl]phosphine}-1,1'-binaphthalene 4

The synthesis was carried out by the reaction of 2,2'-bis (trifluoromethanesulfonyloxy)-1,1'-binaphthalene, 3, with Di[p-(3-phenylpropyl)phenyl]phosphine, 2, to yield 2,2'-Bis{di[p-(3-phenylpropyl)phenyl]phosphine}-1,1'-binaphthalene, 4.

Compound 2 (0.48 g, 1.15 mmol) was added to a solution of NiCl₂(dppe) (0.106 g, 0.2 mmol) in 5 ml DMF at room temperature. The resulting mixture was placed in an oil bath which had been preheated to 100° C. 30 min later a solution of 3 (1.1 g, 2.0 mmol) and DABCO (0.9 g, 8.0 mmol) in 6 ml DMF was added at once. The color of the solution changed immediately to dark brown. Three additional portions of 2 (0.5 g each) were added to the reaction mixture at 1, 3, and 7 h. The solution was kept at 100° C. for 4 days. Most of DMF was removed by vacuum distillation and 40 ml diethyl ether was added to dissolve the organic product. After being washed with 2×20 ml H₂O, either was removed to yield a brown viscous oil. The final product, 4, was separated as a yellow waxy solid from the oil by silica gel column using hexane/diethylether (10/1). The overall yield of the reaction is 45%. 4 was characterized by ¹H, ¹³C, ³¹P NMR and Mass spectrometry.

Analytical data for BINAP-C3

¹HNMR (δ in CDCl₃) 1.87 (m, 8H); 2.53 (m, 8H); 2.59 (m, 8H); 6.7–7.9 (m, 48H).

¹³CNMR (δ in CDCl₃) 32.73 (s, 4C); 35.13 (s, 4C); 35.41 (d,⁵$J_{c-p}$=10.1 Hz, 4C); 125.58 (s, 2C ); 125.71 (s, 4C); 126.24 (s, 2C); 127.51 (s, 2C); 127.91 (s, 2C); 128.16 (s, 4C); 128.26 (s, 8C); 128.41 (s, 8C); 132.92 (*t, 8C); 133.30 (s, 2C); 134.26 (*t, 8C); 135.10 (d, ¹$J_{c-p}$=15.1 Hz, 4C); 136.12 (d, ¹$J_{c-p}$=10.2 Hz, 2C); 141.61 (s, 2C); 142.24 (d, ⁴$J_{c-p}$=3.8 Hz, 4C); 142.50 (s, 4C).

³¹PNMR (δ in CDCl₃) −16.3 (s)

Mass Spectroscopy (FAB, on phosphine oxide) 1127 (M⁺+1)

Step 4 (Scheme 2)

Synthesis of 2,2'-Bis{di[p-(3-p-sulfonatophenylpropyl)phenyl]phosphino}-1,1'-binaphthalene, 5 (=BINAP-C₃-TS)

Compound 4 (1.0 g, 0.9 mmol) was chilled to −78° C. and 8 ml H₂SO₄ (96.1%) was added. The mixture was then allowed to be stirred at room temperature. 10 h later the mixture was neutralized with aqueous NaOH (20%, w/w). The final pH was 8.5. 320 ml of methanol was added and the mixture was brought to reflux for 30 min. The precipitate, NaSO₄, was then filtered and the salt was washed with 100 ml hot methanol. Two portions of the solution were combined and the volume was reduced to 20 ml. 200 ml of acetone was then added to generate a white precipitate. The precipitate, 5, was collected by filtration and dried under vacuum (1.3 g, 95% yield). 5, was characterized by ¹H, ¹³C, ³¹P NMR and Mass spectrometry.

Analytical data for BINAP-C3-TS

¹HNMR (δ in CD₃OD) 1.86 (m, 8H); 2.53 (m, 8H); 2.61 (m, 8H); 6.6–7.9 (m, 44H).

¹³CNMR (δ in CD₃OD) 33.87 (s, 4C); 36.09 (br.s, 8C); 126.28 (s, 2C); 127.13 (s, 8C); 128.38 (s, 2C), 128.75 (s, 2C); 128.88 (s, 2C), 129.32 (br.s, 12C); 134.25 (*t, 8C); 135.44 (*t, 8C); 136.50 (s, 2C); 137.25 (s, 2C); 142.20 (s, 2C); 143.26 (s, 4C); 144.04 (s, 4C); 146.11 (s, 4C).

¹³CNMR (δ in CD₃OD) −15.2 (s)

Mass Spectroscopy (FAB, in glycerol matrix) 1525 (M⁺+ Na⁺)

EXAMPLE 2

Using the procedures outlined in Example 1, steps 2, 3 and 4, the following steps were conducted in order to prepare the chiral form of BINAP-C₃-TS.

Example 2/Step 1

The Synthesis of 2,2'-bis(trifluoromethanesulfonyloxy)-1,1'-binaphthalene(2)

Starting from commercial available (R)-(+)-1,1'-binaphthalene-2,2'-diol, (R)-(−)-2,2'-bis(trifluoromethanesulfonyloxy)-1,1'-binaphthalene (7) was made in one step according to a literature method [18]. The yield of the reaction is 62%.

Example 2/Step 2

The Synthesis of (R)-(+)-2,2'-Bis{di[p-(3-p-sulfonatophenylpropyl)phenyl]phosphino}-1,1'-binaphthalene (6)

The synthesis was carried out according to Cai's Ni catalyzed coupling for the synthesis of 2,2'-bisdiphenylphosphino-1,1'-binaphthyl [reference 19]. The reaction of 2,2'-bis(trifluoromethanesulfonyloxy)-1,1'-binaphthalene (7) with Di[p-(3-phenylpropyl)phenyl]phosphine (2) gives 2,2'-Bis{di[p-(3-phenylpropyl)phenyl]phosphino}-1,1'-binaphthalene 6.

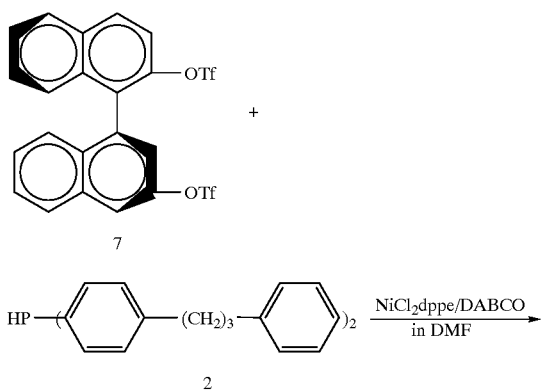

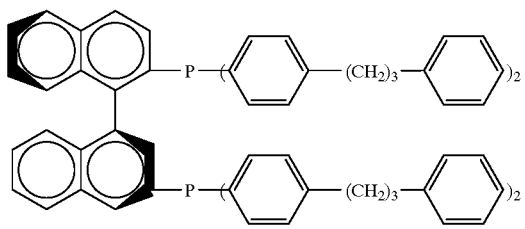

7 and 2 are coupled in the presence of NiCl$_2$(dppe) (dppe=1,2-bis(diphenylphosphino)ethane) and 1,4-diazabicyclo[2.2.2]octane (DABCO) in anhydrous DMF at 100° C. Reaction is complete in 3–4 days. The progress of the reaction is monitored by $^{31}$P NMR. The product, (R)-(+)-2,2'-Bis{di[p-3-phenylpropyl)phenyl]phosphino}-1,1'-binaphthalene (6), is separated by silica gel column using hexane/diethylether (10/1). The overall yield of the reaction is 45%.

The optical purity of 6 is checked by the $^{31}$P NMR spectrum of 2,2'-Bis{di[p-(3-phenylpropyl)phenyl]phosphino}-1,1'-binaphthyl[(S)-N,N-dimethyl-(1-phenylethyl)amine-2C,N]palladium(II). Only (R)-(+)-6 is observed. The spectrum is $^{31}$PNMR (δ in CDCl$_3$) d.d, 20.35, $J_{P\text{-}P}$=43.1 Hz $J_{Pd\text{-}P}$=2146.0 Hz.

Example 2/Step 3

Direct Sulfonation of (R)-(+)-2,2'-Bis{di[p-(3-phenylpropyl)phenyl]phosphino}-1,1'-binaphthalene (6)

The sulfonation of 6 is accomplished by H$_2$SO$_4$ (96%) in 10 hours. Tertrasulfonated product (10) is obtained by precipitation with acetone in minimum amount of water. The yield of sulfonation is 95%.

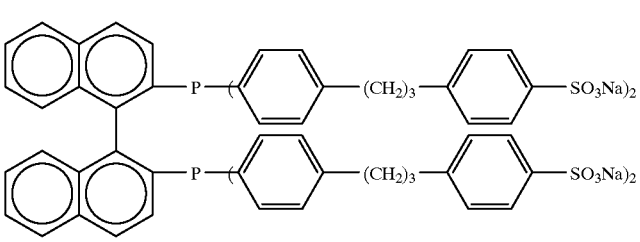

EXAMPLE 3

Step 5 (Scheme 2)

The Synthesis of 2,2'-Bis{di[p-(3-phenylpropyl) phenyl]phosphinomethyl}-1,1'-biphenyl, 11

Di[p-(3-phenylpropyl)phenyl]chlorophosphine 1 (6.0 g, 13.1 mmol) was dissolved in 150 ml THF and Li (0.185 g, 26.2 mmol) was chopped directly into the reaction flask under Ar. A deep red solution was resulted in 10 min and all the lithium was consumed in 4 h. The solution was then filtered and 2,2'-dibromomethyl-1,1'-biphenyl (2.23 g, 6.5 mmol) in 20 ml THF was added dropwise with an ice-water bath. The color of the solution was slowly changed to pale yellow. The mixture was stirred for additional 10 h before the solvent was removed by vacuum. 50 ml diethyl ether was added and it was washed with 3×10 ml $H_2O$. The ether phase was dried over $MgSO_4$ and the solvent was then removed by vacuum. The resulting pale yellow viscous oil was purified over silica gel column. 2.3 g (69% yield) of 11 was eluted with $Et_2O$/hexane (1/10), 11 was characterized by $^1H$, $^{13}C$, $^{31}P$ NMR and Mass spectrometry.

Analytical data for BISBI-C3

$^1$HNMR (δ in $CDCl_3$) 1.83 (m, 8H); 2.51 (m, 16H); 3.06 (*quart, 4H); 6.9–7.2 (m, 44H).

$^{13}$CNMR (δ in $CDCl_3$) 32.72 (d, $^7J_{c-p}$=3.7 Hz, 4C); 33.65 (d, $^1J_{c-p}$=16.1 Hz, 2C); 35.12 (d, $^6J_{c-p}$=2.3 Hz, 4C); 35.31 (d, $^5J_{c-p}$=13.0 Hz, 4C); 125.71 (s, 4C); 128.26 (s, 4C); 128.33 (s, 8C), 128.36 (s, 8C); 129.65 (s, 2C); 129.75 (s, 2C); 132.64 (d, $^3J_{c-p}$=18.3 Hz, 8C); 133.25 (d, $^2J_{c-p}$=19.1 Hz, 8C); 135.18 (d, $^1J_{c-p}$=14.5 Hz, 4C); 135.88 (d, $^3J_{c-p}$=9.2 Hz, 2C); 140.82 (d, $^2J_{c-p}$=4.5 Hz, 2C); 142.09 (s, 4C); 142.44 (s, 4C).

$^{31}$PNMR (δ in $CDCl_3$) –11.8 (s)

Mass Spectroscopy (FAB, on phosphine oxide) 1055 ($M^+$+1)

EXAMPLE 3

Step 6 (Scheme 2)

Synthesis of tetrasulfonated 2,2'-Bis{di[p-(3-phenylpropyl)phenylphosphinomethyl}-1,1'-biphenyl, 12 (=BISBI-$C_3$-TS)

2,2'-Bis{di[p-(3-phenylpropyl)phenyl]phosphinomethyl}-1,1'-biphenyl, 11 (2.2 g, 2.2 mmol), was dissolved in eight ml $H_2SO_4$ (96%) with an ice-water bath. The brown solution was stirred at room temperature for 7 h. The mixture was then neutralized by 20% (w/w) aqueous NaOH. The final pH was 8.5. 320 ml of methanol was added and the mixture was brought to reflux for 30 min. The precipitate, $NaSO_4$, was then filtered and the salt was washed with 100 ml hot methanol. Two portions of the solution were combined and the volume was reduced to 20 ml. 200 ml of acetone was then added to generate a white precipitate. The precipitate, sulfonated 2,2'-Bis{di[p-(3-phenylpropyl)phenyl]phosphinomethyl}-1,1'-biphenyl, 12, was collected by filtration and dried under vacuum (2.8 g, 93% yield). 12 was characterized by $^1H$, $^{13}C$, $^{31}P$ NMR and Mass spectrometry.

Analytical data for BISBI-C3-TS $^1$HNMR (δ in $CD_3OD$) 1.91 (m, 8H); 2.57 (m, 8H); 2.63 (m, 8H); 3.10 (*quart, 4H); 6.8–7.8 (m, 40H).

$^{13}$CNMR (δ in $CD_3OD$) 34.12 (d, $^1J_{c-p}$=13.1 Hz, 2C); 34.15 (s, 4C); 36.13 (s, 4C); 36.20 (s, 4C); 127.08 (s, 8C); 129.36 (s, 8C); 129.77 (s, 4C); 130.70 (s, 2C); 130.75 (s, 2C); 133.75 (d, $^3J_{c-p}$=18.3 Hz, 8C); 134.51 (d, $^2J_{c-p}$=19.8 Hz, 8C); 143.92 (s, 4C); 146.15 (s, 4C).

$^{31}$PNMR (δ in $CD_3OD$) –10.7 (s)

Mass Spectroscopy (FAB, in glycerol matrix) 1453 ($M^+$+ $Na^+$)

EXAMPLES 4 and 5

Two Phase Catalysis with 2,2'-Bis{di[p-(3-p-sulfonatophenylpropyl)phenyl]phosphino}-1,1'-binaphthalene (BINAP-$C_3$-TS) 5 and 2,2'-Bis{di[p-(3-p-sulfonatophenylpropyl)phenyl]phosphinomethyl}-1,1'-biphenyl (BISBI-$C_3$-TS) 12

EXAMPLE 4

Two phase hydroformylation of 1-octene with BINAP-$C_3$-TS and BISBI-$C_3$-TS

Two phase hydroformylation of 1-octene with BISBI-$C_3$-TS and BINAP-$C_3$-TS was carried out in a 30 ml stainless steel reaction vessel. The catalyst was made in situ by mixing 0.76 ml 0.01 M Rh(acac)(CO)$_2$ in methanol and the required amount of 0.1 M aqueous solution of ligand. Water was added to adjust the total aqueous methanol volume to 1.56 ml. The substrate, 0.60 ml of 1-octene, was then transferred into the reaction vessel under positive pressure of CO. Nonane, 0.40 ml, was added as an internal standard for gas chromatography analysis. Therefore, the volume of organic phase is 1.0 ml. The octene/Rh ratio was 500/1 in all catalytic runs. After the reaction vessel was loaded and pressurized with CO/H$_2$ to 210 psi, the reaction was initiated by placing the reaction vessel into a temperature bath preheated to 120° C. The reaction mixture was constantly stirred with a magnetic stir bar at 350 rpm. Catalytic reactions were terminated by removing the vessel from the oil bath and depressurizing when it had been cooled in an ice-water bath. In all cases the organic layer was colorless and readily separated from aqueous layer after the reaction.

The reaction product distribution was analyzed by gas chromatography on a Varian 3300 gas chromatograph equipped with a HP1 column 25 m×0.32 mm×0.52 μm, and FID detector, He was the carrier gas; the temperature program was from 35° C. (4 min) to 220° C. (1 min), at a heating rate of 10° C./min. A special injection port sleeve was installed to facilitate the separation of analytes which have very close boiling points.

Hydroformylation results of 1-octene with BISBI-$C_3$-TS and BINAP-$C_3$-TS are summarized in Table 1. For comparison, results from two phase hydroformylation of 1-octene with TPPTS under the same reaction conditions is also listed. The aqueous solution consists of 50% H$_2$O and 50% methanol. The presence of methanol is due to the preparation of in situ catalyst. Leakage of methanol into the organic phase after the reaction is less than 0.5%. Concentration of Rh in both the organic and aqueous phases was checked by ICP method (Table 2). The detection limit is ~⅓ ppm. The organic phase after the reaction is without color and Rh is not detected by ICP, which since the sample is diluted, sets a lower limit of 3ppm on Rhodium in the organic phase if it indeed is present.

At ligand/Rh ratio of 7–9, the rhodium catalyst with BISBI-$C_3$-TS offers good reactivity and selectivity towards 1-nonanal. Detailed product distribution is given in Table 2. Increased activity, compared to the Rh/TPPTS system, is understandably explained by the surface activity of the ligand.

TABLE I

Two Phase Hydroformylation of 1-octene
with BISBI-C₃-TS, BINAP-C₃-TS and TPPTS

| | TPPTS | | BISBI-C3-TS | | BINAP-C3-TS | |
|---|---|---|---|---|---|---|
| Rh/P ratio | Yield (%) | n/b (%/%) | Yield (%) | n/b (%/%) | Yield (%) | n/b (%/%) |
| 1:2 | 30 | 68/32 | 45 | 68/32 | 29 | 74/26 |
| 1:3 | 37 | 70/30 | 57 | 76/24 | 31 | 74/26 |
| 1:5 | 52 | 75/25 | 69 | 88/12 | 14 | 75/25 |
| 1:7 | 54 | 76/24 | 73 | 94/6 | 5.3 | 70/30 |
| 1:9 | 69 | 76/24 | 67 | 97/3 | — | — |
| 1:14 | — | — | 30 | 98/2 | — | — |

Reaction Conditions: reaction time, 5 h; reaction temperature, 120° C.; initial pressure, 210 psi (at 25° C.); stirring rate is 350 rpm; [Rh] = 0.0049 M.

TABLE 2

Results From Two Phase Hydroformylation of Octene-1 at Rh/Phosphorus = 1/7. Product Distribution

| | TPPTS | BISBI-C₃-TS |
|---|---|---|
| yield of C₉ aldehydes (%) | 58 | 74 |
| selectivity (% of 1-nonanal) | 74 | 93 |
| C₈ hydrocarbons (%) | 34 | 23 |
| [% of 1-octene] | [5] | [14] |
| C₉ alcohols (%) | 7.1 | 2.5 |
| heavy ends (%) | 0.8 | 0.2 |
| [Rh] in organic phase (ppm) | not detected | not detected |
| [Rh] in aqueous phase (ppm) | 508 | 514 |

Reaction conditions: [Rh] = 502 ppm, Rh/octene-1 = 1/500, Temperature = 120° C., Pressure = 210 psi at room temperature, Reaction time = 5 h, Stirring rate = 350 rpm, The [Rh] is determined by ICP method. Both standard and samples are prepared in MeOH.

EXAMPLE 6

Two phase asymmetric hydrogenation of acetophenone N-benzylimine with (R)-(+)-BINAP-C₃-TS (6)

Hydrogenation of acetophenone N-benzylimine with (R)-(+)-BINAP-C₃-TS (6) is carried out under two phase conditions with ethyl acetate as the organic solvent.

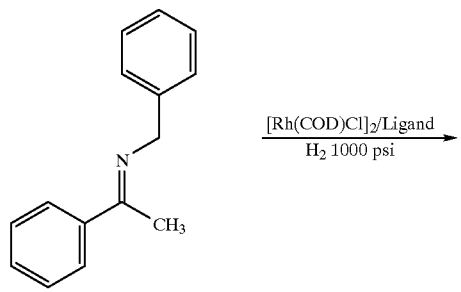

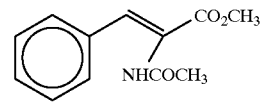

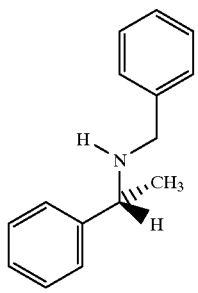

The catalyst is made in situ by mixing [Rh(COD)Cl]₂ with water soluble ligand in water. The substrate, acetophenone N-benzylimine, is dissolved in ethyl acetate and charged to the reactor after the catalyst is totally dissolved in water, which takes about 10 min. The reactor is then pressurized to 1000 psi of H₂. The reaction temperature is 25° C. and the reaction time is 41.5 hours. The same catalysis with Rh/tetrasulfonated (2S, 4S)-bis-(diphenylphosphino)pentane (BDPPTS) is also done for comparison. The conversion is checked by GC-MS and ¹H NMR. The optical purity of the product is determined by ¹H NMR using 2,2,2-trifluoro-1-(9-anthryl)ethanol as shift reagent.

TABLE 3

Asymmetric Hydrogenation of acetophenone N-benzylimine with (R)-(+)-BINAP-C₃-TS and (2S, 4S)-BDPPTS

| Ligand | Yield (%) | e.e. (%) |
|---|---|---|
| BINAP-C₃-TS | 98 | 56 |
| BDPPTS | 45 | 29 |

Compared to Rh/BDPPTS catalyst, rhodium catalyst with BINAP-C₃-TS offers increased activity and selectivity.

Asymmetric hydrogenation with (R)-(+)-BINAP-C₃-TS

According to Example 6, 2-(4-isobutylphenyl) propanoic acid and the methyl ester of acetylaminocinnamic acid were asymmetrically hydrogenated with the Rh- or Ru complexes of (R)-(+)-BINAP-C₃-TS (Table 4).

TABLE 4

Asymmetric Catalysis Results with (R)-(+)-BINAP-C₃-TS

| Catalyst | Substrate | Conversion | e. e (%) |
|---|---|---|---|
| Ru/BINAP-C₃-TS | 2-(4-isobutylphenyl)propenoic acid | 100 | 19 |
| Rh/BINAP-C₃-TS | ![styrene derivative with CO₂CH₃ and NHCOCH₃] | 100 | 16 |

The quantitative conversion of substrates clearly proves the concept of surface active ligands, which allow catalytic reaction in a two-phase media like water-insoluble substrates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing an aryl diphosphine which comprises the steps of (a) subjecting an arylphosphine halide to metallation conditions including suitable temperature and pressure to form an arylphosphinide, and (b) subjecting said formed arylphosphinide, to coupling conditions including suitable temperature and pressure in the presence of an organic halide to form said aryl diphosphine.

2. The process as set forth in claim 1 wherein the aryldiphosphine produced has the formula

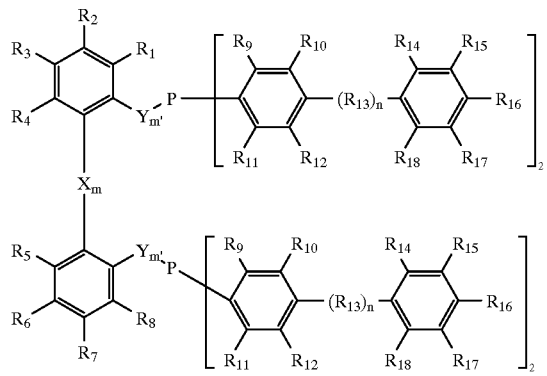

wherein (a) X and Y are each independently selected from the group consisting of alkyl $C_1$–$C_{20}$, alkenyl $C_1$–$C_{20}$, alkynyl $C_1$–$C_{20}$, phenyl, naphthyl, —NR— (where R is H, alkyl $C_1$–$C_{20}$, phenyl), oxygen and sulfur; (b) m and m' are each separate integers of 0 or 1; (c) $R_1$–$R_8$ are each independently selected from the group consisting of hydrogen, halogen, nitro, amino, alkyl $C_1$–$C_{20}$, alkoxy, hydroxy —C(O)—OR, —CN, —$SO_3$M, —$N^\ominus$ $(R)_3$ $X^\ominus$ (where $X^\ominus$ is a halide), and aryl; (d) $R_1$ and $R_2$, $R_2$ and $R_3$, $R_3$ and $R_4$, $R_5$ and $R_6$, $R_6$ and $R_7$, $R_7$ and $R_8$ may also (in addition to the above) from a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; (e) $R_9$–$R_{12}$ and $R_{14}$–$R_{18}$ are each independently selected from the group consisting of hydrogen, halogen, —$SO_3$M where M is selected from the group of alkali metal, alkaline earth metals, and $N(R)_4^\oplus$ (where R is H, alkyl $C_1$–$C_{20}$, phenyl), alkyl $C_1$–$C_{20}$, —$CO_2$M, —$N^\oplus$ $(R)_3$ $X^\ominus$ (where $X^\ominus$ is a halide), —CN, —OR, —C(O)—OR, and —$P(R)_2$, where R is H, alkyl $C_1$–$C_{20}$, and phenyl; (f) $R_{13}$ is selected from the group consisting of a straight chain or branched chain alkyl $C_1$–$C_{20}$, alkenyl $C_1$–$C_{20}$, alkynyl $C_1$–$C_{20}$, phenyl, naphthyl, anthracyl, and substituted phenyl, naphthyl, and anthryl; and (g) n is an integer from 0 to 20.

3. A process for preparing an aryl diphosphine of the formula

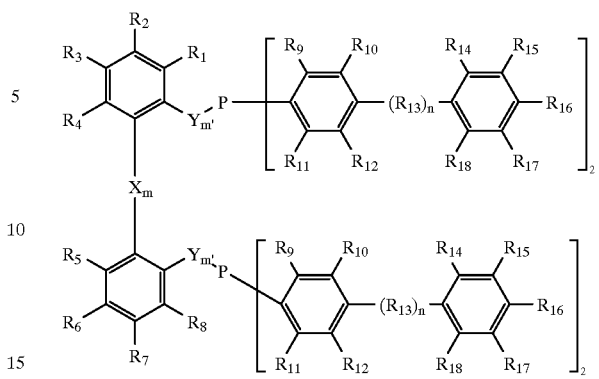

wherein (a) X and Y are each independently selected from the group consisting of alkyl $C_1$–$C_{20}$, alkenyl $C_1$–$C_{20}$, alkynyl $C_1$–$C_{20}$, phenyl, naphthyl, —NR— (where R is H, alkyl $C_1$–$C_{20}$, phenyl), oxygen and sulfur; (b) m and m' are each separate integers of 0 or 1; (c) $R_1$–$R_8$ are each independently selected from the group consisting of hydrogen, halogen, nitro, amino, alkyl $C_1$–$C_{20}$, alkoxy, hydroxy-C (O)—OR, —CN, —$SO_3$M, —$N^\ominus$ $(R)3$ $X^\ominus$ (where $X^\ominus$ is a halide), and aryl; (d) $R_1$ and $R_2$, $R_2$ and $R_3$, $R_3$ and $R_4$, $R_5$ and $R_6$, $R_6$ and $R_7$, $R_7$ and $R_8$ may also (in addition to the above) from a cyclic ring containing a total of 2 to 6 atoms selected from the group consisting of carbon atoms, oxygen atoms, nitrogen atoms, sulfur atoms, and mixtures thereof, with the proviso that said ring can be substituted or unsubstituted; (e) $R_9$–$R_{12}$ and $R_{14}$–$R_{18}$ are each independently selected from the group consisting of hydrogen, halogen, —$SO_3$M where M is selected from the group of alkali metal, alkaline earch metals, and $N(R)_4^\ominus$ (where R is H, alkyl $C_1$–$C_{20}$, phenyl), alkyl $C_1$–$C_{20}$, —$CO_2$M, —$N^\ominus$ $(R)_3$ $X^\ominus$ (where $X^\ominus$ is a halide), —CN, —OR, —C(O)—OR, and —$P(R)_2$, where R is H, alkyl $C_1$–$C_{20}$, and phenyl; (f) $R_{13}$ is selected from the group consisting of a straight chain or branched chain alkyl $C_1$–$C_{20}$, alkenyl $C_1$–$C_{20}$, phenyl, naphthyl, anthracyl, and substituted phenyl, naphthyl, and anthryl; and (g) n is an integer from 0 to 20 which comprises the steps of (a) subjecting an arylphosphine halide to matallation conditions including suitable temperature and pressure to form an arylphosphinide, and (b) subjecting said formed arylphosphinide, to coupling conditions including suitable temperature and pressure in the presence of an organic halide to form said aryl diphosphine and wherein after step (b), the aryl diphosphine is subjected to step (c) which comprises the reaction of said aryldiphosphine with an acid base condition to form a water-soluble aryldiphosphine.

* * * * *